(12) United States Patent
Chinnock et al.

(10) Patent No.: US 7,130,047 B2
(45) Date of Patent: Oct. 31, 2006

(54) METHOD OF PRODUCING POLARIZERS FOR POLARIZED OPTICAL PROBES

(75) Inventors: Randal B. Chinnock, Southbridge, MA (US); Jeffrey S. Melanson, Sturbridge, MA (US)

(73) Assignee: Optimum Technologies, Inc., Southbridge, MA (US)

( * ) Notice: Subject to any disclaimer, the term of this patent is extended or adjusted under 35 U.S.C. 154(b) by 0 days.

(21) Appl. No.: 11/245,846

(22) Filed: Oct. 7, 2005

(65) Prior Publication Data

US 2006/0050273 A1 Mar. 9, 2006

Related U.S. Application Data

(63) Continuation-in-part of application No. 10/835,747, filed on Apr. 30, 2004.

(51) Int. Cl.
*G01J 4/00* (2006.01)
(52) U.S. Cl. ...................................... 356/364
(58) Field of Classification Search ............... None
See application file for complete search history.

(56) References Cited

U.S. PATENT DOCUMENTS

| 6,049,377 A * | 4/2000 | Lau et al. ..................... 356/73 |
| 6,362,619 B1 * | 3/2002 | Prammer et al. ........... 324/303 |
| 6,816,261 B1 * | 11/2004 | Patel et al. ................. 356/365 |

* cited by examiner

*Primary Examiner*—Tu T. Nguyen
(74) *Attorney, Agent, or Firm*—Brian M. Dingman, Esq.; Mirick, O'Connell, DeMallie & Lougee, LLP

(57) ABSTRACT

Methods of creating tooling designs for, and the production of, one or more polarizer groups on a workpiece. Each such group includes an optically transmitting substrate with one or more discrete polarizer pixels thereon. The polarizer groups are used with optical instruments having a number of optical channels. In the method, one or more physical characteristics of at least one optical channel of the optical instrument are measured. Based on the determined physical characteristics, one or more discrete polarizer groups to be created on the substrate are defined, by defining for each such group a location on the substrate for the group, the size, shape and location within the group of each polarizer pixel of the group, and the polarization orientation for each such polarizer pixel of the group. The area of each polarizer pixel is then filled with tooling information that will establish its polarization orientation.

38 Claims, 6 Drawing Sheets

METHOD OF PRODUCING POLARIZERS FOR POLARIZED OPTICAL PROBES

CROSS-REFERENCE TO RELATED APPLICATION

This application is a continuation in part of application Ser. No. 10/835,747, filed on Apr. 30, 2004. Priority is claimed.

GOVERNMENT RIGHTS

This invention was made with Government support under Grant Number 1 R 43 CA103083-01 awarded by the National Institutes of Health (NIH). The Government has certain rights in the invention.

FIELD OF THE INVENTION

This invention relates to methods of making polarizers for polarized optical probes.

BACKGROUND OF THE INVENTION

Methods of Optical Analysis

Photons from the ultraviolet, optical, and infrared portions of the electromagnetic spectrum have been used for over 100 years to investigate the properties of matter. These techniques, hereinafter referred to as "methods of optical analysis", include but are not limited to Raman spectroscopy, infrared (IR) spectroscopy, atomic absorption spectroscopy, diffuse reflectance spectroscopy, fluorescence spectroscopy, photoluminescence spectroscopy, and elastic scattering spectroscopy.

In Raman spectroscopy, a sample is irradiated with a substantially monochromatic light source. A small percentage of the incident photons absorbed by the sample are instantaneously re-emitted at slightly different wavelengths. These shifts in wavelength, referred to as Stokes or anti-Stokes shifts, result from changes in the rotational and vibrational states of the constituent molecules. The emitted spectra, captured in a backscattered configuration and analyzed with the spectrometer, reveal very specific information about the chemistry and structure of the sample, particularly information related to carbon-carbon bonds.

IR spectroscopy is similar to Raman, but operates at longer wavelengths. The method is sensitive to functional group vibrations especially OH stretch in water, and is good for studying the substituents on organic molecules. Also, the method can use the unique collection of absorption bands to confirm the identity of a pure compound or to detect the presence of specific impurities Fluorescence spectroscopy is similar to Raman spectroscopy, in that a sample is irradiated with a substantially monochromatic light source and the re-emitted spectra is captured and analyzed by a spectrometer. However, in the case of fluorescence the emitted spectrum is derived from certain electronic transitions in the sample's constituent molecules. This spectrum is broader and more intense than Raman spectra, lacks Raman's fine structure, and occurs over an extended time frame. Fluorescence spectroscopy is used to determine the chemical constituents of a sample.

In diffuse reflectance spectroscopy (DRS), a broadband light source irradiates a turbid, translucent, or opaque sample. Certain wavelengths of light are selectively absorbed by the sample, and some are scattered. A spectrometer configured to capture backscatter analyzes the spectrum of the scattered rays. "Dips" in the spectrum, caused by absorption in the sample, reveal information about the molecular content of the sample.

In DRS, scattered photons captured by the spectrometer may have undergone elastic or inelastic scattering, or both. Elastic scattering spectroscopy (ESS) is similar to DRS, except that the geometry of the optical system is controlled so that only rays that have undergone high-angle elastic scattering are captured by a spectrometer. Mie scattering theory may then used to analyze the spectra. These spectra reveal information about the size of the scatterers, their index of refraction, the average distance between scatterers, and ranges of values on these measures. This technique has been used to analyze industrial materials such as slurries containing liquids and suspended particles. It has also been used to assess biological tissues. In this case, the ESS spectrum reveals the size of intracellular components such as nuclei and mitochondria. Enlargement of these components above normal levels may indicate a disease state such as cancer. The technique also reveals changes in chromatin density and granularity that may be associated with dysplasia.

In atomic absorption spectroscopy, a broadband light source and a spectrometer are arranged in an "opposed" configuration (facing each other) to measure gas-phase atoms. Since the samples of interest are usually liquids or solids, the analyte atoms or ions must be vaporized in a flame or graphite furnace in order to be analyzed. The atoms absorb ultraviolet or visible light and make transitions to higher electronic energy levels. The analyte concentration is determined from the amount of absorption as the light passes through the vaporized sample. This technique is capable of detecting very small concentrations of atoms or molecules in a sample.

Fourier transform (FT) techniques may alternatively be used with many of the optical analysis methods described above. FT techniques convert a time domain measurement to a frequency domain measurement, or vice versa. Instruments employing FT basically reveal the same information about a sample as a comparable instrument without FT, but an FT instrument may be optimized for higher resolution, higher speed, higher sensitivity, or other parameters.

The Use of Polarization in Optical Analysis Techniques

The term "polarization" refers to the spatial orientation of each photon's electromagnetic field relative to its direction of travel. Most naturally-occurring and manmade light sources produce photons with random polarization states. Lasers are generally highly polarized. In all of the optical analysis methods described above, non-polarized light may be used. However, with some of these techniques, the use of polarized light may enable benefits such as higher sensitivities, improved signal-to-noise ratios (SNRs) or additional capabilities.

For example, polarized atomic absorption spectroscopy systems such as the Hitachi Z-5000 offer lower detection limits with a smaller, simpler instrument design compared to non-polarized instruments.

Polarized Raman spectroscopy is used, for example, to determine the secondary and tertiary structures of membrane proteins in biological samples. By studying these aligned proteins with polarized Raman spectroscopy, additional data about the orientation of the bond-polarizability tensors with respect to the known polarization direction of the lazer is obtained. This information is combined with molecular models to infer details about the structure of the protein.

In the materials science field, optical strain gauges may also employ polarized Raman spectroscopy. Sensors are constructed by embedding carbon nanotubes in a polymer. Polarized Raman analysis is very sensitive to the strain transferred from the matrix to the nanotubes.

External Reflection Spectroscopy (IRRAS) is used to examine thin films on mirror-like substrates such as coatings and adhesives on metal surfaces. Using a grazing angle technique, the beam makes a high-angle reflection of approximately 88° from the sample and is polarized in the plane of incidence (p-polarization). Polarization sensitivity makes IRRAS useful in determining the orientation of molecules in relation to the metal.

In the polarized variant of ESS (PESS), a polarized broadband source is used to irradiate a sample such as biological tissue. Instead of the single optical channel used to measure the backscattered light in ESS, two channels are used in PESS. One channel is linearly polarized with the same spatial orientation as the source channel, while the other channel is cross-polarized. Since the polarization of backscattered photons depends on the number of scattering events the photon has undergone, and their subtended scattering angle, this detection method collects photons mostly from a well-defined region of the tissue and filters out many of the photons scattered from underlying and surrounding tissue. This enables measurements with high spatial sensitivity and high signal-to-noise ratio. Recent clinical studies have demonstrated the utility of PESS for the analysis of the surface layers of human tissues lining the outside of the body and body canals (epithelia). Carcinomas originate in epithelial layers, so sampling of this layer independently of the sub-epithelial layers enables the detection of atypical tissues at the earliest stages of growth. ESS and PESS investigations are currently being conducted in many parts of the body, including the gastrointestinal tract (oral cavity, esophagus, stomach, intestines), mammary ducts, bladder, urethra, cervix, and skin.

Fiberoptic Sampling Probes

In many applications, it is desirable to measure a sample in situ, rather than removing a sample from its original location for analysis in a laboratory. Examples in the medical field include measurements of human or animal tissue in vivo, either on the surface of the body, just below the surface using a percutaneous technique, or deep inside the body using an endoscope. Pharmaceutical and cosmetic applications include measurements of powders, slurries, suspensions, and solids. Environmental applications include field measurements of water in lakes and streams, and gases in smokestack emissions. Industrial applications include process control measurements in locations such as chemical plants, oil refineries, food processing plants, breweries, and fuel depots. Public safety, security, and forensic applications include detection of explosives residue, illegal drugs, and biohazards such as biological warfare agents, toxic chemicals, and microbial contamination.

In a number of these applications, physical access to the sample is limited. For example, in a lake it may be desired to take a measurement at a depth of 2 meters. In the body, a sample may be required deep in the esophagus. In a cosmetics factory, a sample may be required of a slurry inside a vat or flowing in a pipe. For many of these applications, it may not be possible or economical to bring the analytical instrument to the sample. Instead, fiberoptic probes often provide the optimal means of conveying light from the instrument to the sample, and/or from the sample to the instrument. Fiberoptic probes are efficient conductors of broadband light, are immune to electromagnetic interference, can be very long (up to hundreds of meters in length), and may be constructed to be flexible, with very small cross sections that can fit into tiny spaces.

Polarized Fiberoptic Probes

Implementing polarized detection in fiberoptic probes has advantages, but had historically been difficult to implement. Following is a discussion of issues pertaining to the use of fiberoptic probes for Polarized ESS (PESS). However, the main points of the discussion are also applicable to the other optical analysis methods discussed above, and are intended to illustrate the general case.

There are several design difficulties in trying to make small-diameter PESS probes suitable for certain applications, especially in the medical field for needle- or endoscopic-delivery in-vivo.

In order for PESS to work properly, broadband polarized light must be delivered to a sample, and two detection channels must conduct broadband light to spectrometers for analysis of the scattered light. The two detection channels must have orthogonal polarizations with high extinction ratios (at least 10:1, and preferably >100:1). Achieving high extinction ratios for two polarization modes over broad passbands is the principal challenge. For the PESS application, "broadband" means a passband of about 600 nm. For other applications, "broadband" may mean a passband as narrow as 20 nm.

Fabricating polarized optical probes may be approached in two ways. FIG. 1 shows the first approach. An analysis instrument 1 is optically coupled 2 to an optical probe 3. The probe contains one delivery channel 4 and two collection channels 5 and 6. The probe is in optical communication 7 with tissue or another type of sample 8. The polarizers 9 are placed between the probe 3 and instrument 1, and polarize the light as it is transmitted. This is the easier approach because the polarizers are inside the analysis instrument instead of being part of the probe, and so there is little constraint on their size or cost. However, with this arrangement the optical channels 4, 5 and 6 must maintain the polarization of the incident light as the light propagates along the length of the probe 3. If the channels are constructed using conventional optical fiber, polarization is lost, thus invalidating the measurement. While fibers that maintain the polarization state of transmitted light ("polarization-maintaining fibers") exist, they only offer acceptable performance over a maximum passband on the order of 20 nm. They are thus unsuitable for optical analysis methods employing broadband light.

The optimum optical architecture for PESS and other polarization-based architectures is to place the polarizers at the sample end of the probe. This is advantageous, as the light is polarized as it exits the delivery fiber on its way to the sample, and the scattered light is polarized as it enters the detection fibers. Since only light of the correct polarization enters each detection channel, loss of polarization as the light propagates along the length of the channel does not affect the measurement. This allows the probe to be constructed, for example, with relatively low-cost, commercially available broadband fiber (such as silica-clad-silica).

Nevertheless, this approach presents a number of difficulties. First, for the PESS application, since the probe is mainly intended for measurements of epithelial tissues, it is desirable to confine the sensing volume to the first 300 microns of tissue depth. This constrains the optical geometry of the distal tip—the delivery and collection fibers must be separated by no more than a few hundred microns, and their end faces must be in very close proximity to the tissue. To eliminate crosstalk caused by Fresnel reflections (i.e., light leakage from one optical channel to another caused by reflections from optical surfaces), any polarizer placed between the fibers and the tissue must have a thickness significantly less than the spacing between the fibers. This puts further constraints on the size and shape of the polarizers, as well as the fibers.

To be commercially viable, a single-use medical probe must also have a low manufacturing cost. This eliminates the use of any fabricated parts that have a high labor content. If the probe is reusable, the manufacturing cost can be higher, but the probe must withstand high temperature sterilization by steam autoclave. This puts additional constraints on materials, adhesives and optical coatings.

None of the conventional polarizer technologies has the necessary characteristics for this application. Dielectric thin film cube beam splitters rely on the difference in the reflectance of S and P polarization states with angle. This means that the surface on which the coating is deposited must be mounted at an angle to the optical axis. This is typically achieved by depositing the polarizing coating onto a 45° surface inside a cube beam splitter. Unpolarized light is split into S and P components at the 45° surface. However, placing a tiny cube at the sample end of a small diameter probe presents several difficulties. First, because the ray bundles exiting the delivery channels diverge, the cube must be significantly larger than the channel diameter, driving the overall probe size up. This makes its use infeasible in certain applications, especially certain parts of the body. Second, the cross-polarized collection channel requires the use of a second cube that is rotated 90° to the aligned cube. This complicates the design and increases the probe size further. For these reasons, probes using dielectric thin film cube beam splitters are typically in the range of 1"–4" in diameter. Third, in order to prevent Fresnel reflections from the sample side of the beam splitter cubes, those optical surfaces must either be tilted or coated with a high efficiency anti-reflection coating, further increasing complexity and cost. The use of cube beam splitters thus does not lead to a commercially-viable disposable probe manufacturing cost in any volume.

Dichroic Sheet Polarizers have also been used by some researchers to construct fiberoptic probes. "Dichroism" is selective absorption of one polarization plane over the other during transmission through a material. Sheet-type dichroic polarizers are generally manufactured using films of organic materials. The film is stretched, aligning molecules into a birefringent geometry, and then dyed. The dye molecules selectively attach themselves to aligned polymer molecules, so that absorption is high in one plane and weak in the other. The stretched film is then bonded to a transparent substrate or sandwiched between a pair of sheets (glass, plastic, fused silica, etc.) to stabilize it and protect it from the environment. The transmitted beam is linearly polarized. Polarizers made of such material are very useful for low-power and visual applications. The main advantages of this type of polarizer are good performance vs. angle of incidence and thin substrate thickness. However, there are several problems with using dichroic polarizers for fiberoptic probes. First, none of the organic compounds used in these polarizers remains stable when exposed to the temperatures required for steam autoclave (>120° C.). Since steam autoclaving is the most common method of sterilizing reusable medical devices, this is a major impediment to commercialization. Second, none of the dichroic polarizers has the desired spectral bandwidth. Some are optimized for the UV, some for the visible, but none for both. This limits the clinical utility of the probe. Third, though the dichroic sheet polarizers have the shortest optical path of any polarizer, the commercially available ones are still too thick (~200 microns—Polaroid Corp.). This results in Fresnel reflections from the sample side of the polarizer, which compromises signal to noise ratio. Fourth, it is difficult to cut, handle, and bond such a tiny disk of filter material to the end of a fiber probe. Because the films have been stretched in one axis, when mounted on thin substrates, these polarizers curl very strongly, contributing to difficulties in handling. This is exacerbated by the fact that tiny pieces of the film must be mounted with their polarization axes orthogonal to each other. Fifth, since the bonding area is so small, the polarizers could detach, especially if prone to curling, and especially if the probe is used multiple times. If they detached in-vivo, this could pose a health hazard.

Birefringent crystal polarizers have also been considered, but the crystals are typically in the range of several millimeters thick, making them impractical for small diameter probes. They are also too fragile to be placed at the distal end of a probe, and are too expensive for typical commercial applications, especially disposable devices.

Wire grid array polarizers use a periodic series of parallel wires etched or deposited onto a substrate, as described in U.S. Pat. No. 6,122,103. This array passes one polarization mode and reflects the orthogonal one. It offers very high transmission, high extinction, large acceptance angle, high temperature tolerance, and may be used oriented normal or inclined to the optical axis. Semiconductor lithographic methods are used to form the array of wires on the transparent substrate. However, commercial wire grid polarizers are typically deposited on substrates several mm thick. Using such a thick polarizer at the distal end of a small diameter probe would result in unacceptable performance due to Fresnel reflections. Also, wire grid polarizers have been used mainly in the display industry. Thus, the substrates typically have a large area, all with the same polarization orientation. This arrangement is called a "sheet polarizer".

For macro-sized optical systems employing individual free space optical elements, polarization management usually presents no problem, since individual polarizers may be placed in various parts of the beam path to achieve the desired result. In this case, conventional, macro-sized polarizers suffice. However, there are cases where the packaging constraints on the system prohibit the use of macro-sized optical elements, for example, where the optical system is designed to measure the characteristics of fluids in a narrow pipe. Further, there are cases where the geometry of individual optical channels themselves prohibits the use of macro-sized optical elements, as in a system where individual optical fibers comprise the separate optical channels.

Micro-optical systems are designed to operate in extremely small spaces, e.g., in the human body. For such micro-optical systems, optical channels may be spaced apart by as little as tens of microns. These channels are often formed by fiberoptics. Channels may be arranged in a linear fashion, in circles, or any fixed or random pattern. For certain optical systems it is necessary to polarize the light passing through these optical channels. Furthermore, adjacent channels may require different polarization orientations. A method is therefore needed to create a polarizer with multiple pixels with different polarization orientations. Conventional polarizer manufacturing technology cannot produce multiple polarizer pixels on a single substrate with the small size and placement accuracy necessary to reliably separate the individual channels.

In sum, none of the existing polarizer technologies has the combination of bandwidth, small size, thinness, low cost, durability, sterilizability, or ability to be formed into discrete elements (pixels) that would enable the construction of small diameter polarized probes. In addition, none of the polarizer technologies discussed is manufactured via processes that easily lend themselves to "mass customization", i.e., the production of large numbers of components that all have similarities, but unique differences as well.

SUMMARY OF THE INVENTION

The present invention pertains primarily to the manufacturing of polarizer groups for an optical probe with one or more optical channels. The process makes novel use of polarizer manufacturing technologies that allow polarizer groups to be adaptably "pixelated" at the appropriate size and position to create small polarizer groups that can be mounted in a durable and cost-effective fashion on the probe (generally at its sample end).

This invention relates to the field of creating customizable multiple polarizer pixels on a single substrate. Each area is termed a polarizer "pixel", while a collection of one or more such polarizer pixels on a common substrate, for use with an optical probe, is termed a polarizer "group." The polarizer groups can be used with optical probes having one or more separate optical channels, to accomplish separate polarizations of light, such as discussed above. The optical channels may include one or more illumination (delivery) channels, one or more sensing or collecting channels, and/or one or more reference channels.

This invention helps to accomplish a variably-polarizing optical probe assembly having one or more optical light delivery channels that emit incident light from the sample end of the probe toward a sample being investigated, and one or more optical light-receiving channels that receive incident light from the sample. The assembly further comprises a polarizing group, which itself is comprised of an optically transmitting substrate and one or more discrete polarizer pixels on the substrate, each such polarizer area or "pixel" defining a polarization orientation, with the polarizer pixels together preferably defining at least two polarization orientations. The polarizer group is coupled to the sample end of the probe such that one polarizer pixel covers at least one light delivery channel and a different polarizer pixel covers at least one light-receiving channel.

This invention also helps to accomplish a variably-polarizing polarizer group for polarizing light emitted from the sample end of one or more light delivery channels of an optical probe, and the light received into one or more light-receiving channels of the optical probe, the group comprising an optically transmitting substrate and at least two discrete polarizer pixels on a face of the substrate, each such polarizer pixel defining a polarization orientation, with the polarizer pixels together defining at least two different polarization orientations.

The invention further helps to accomplish a variably-polarizing polarizer group for polarizing the light received by or emitted from a device, comprising an optically transmitting substrate and at least two discrete polarizer pixels on a face of the substrate, each such polarizer pixel defining a polarization orientation, with the polarizer pixels together defining at least two different polarization orientations. The device may comprise an image sensor, to accomplish polarized imaging with a single image sensor.

This invention features methods of creating tooling designs for, and the production of, one or more polarizer groups on a workpiece. Each such group includes an optically transmitting substrate with one or more discrete polarizer pixels thereon. The polarizer groups are used with an optical instrument having a number of optical channels. One or more physical characteristics of at least one optical channel of the optical instrument are measured. Based on the determined physical characteristics; one or more discrete polarizer groups to be created on the substrate are defined. For example, a location on the substrate for the group; the size, shape, and location within the group of each polarizer pixel of the group; and the polarization orientation for each such polarizer pixel of the group may be specified. The area of each polarizer pixel is then filled with tooling information that specifies its polarization orientation. Alternatively, the information may be formatted as vector, bitmap, or other file types.

Also featured in the invention is a method of creating a tooling design for the production of a workpiece comprising an optically transmitting substrate having thereon a plurality of polarizer groups, each polarizer group comprising a plurality of discrete polarizer pixels, the polarizer groups for use in an optical instrument comprising a plurality of separate optical channels, the method comprising determining the relative locations and shapes of the optical channels of the optical instrument, based on the determined relative locations and shapes of the optical channels, defining one or more discrete polarizer groups to be created on the substrate, defining for each such group a location on the substrate, the size, shape and location within the group of each polarizer pixel of the group; and the polarization orientation for each such polarizer pixel of the group. The area of each polarizer pixel is filled with tooling information that specifies its polarization orientation. The workpiece is then manufactured from this tooling information using a lithographic process.

The polarizer pixels may comprise wire grid array polarizers or dichroic polarizers formed with nano crystals or polarizers formed by another means. The polarizer is preferably less than about 200 microns thick, though for some optical geometries may need to be as little as 30 microns thick. It may have an anti-reflection coating on the sample side to minimize Fresnel reflections. The polarizer may be optimized for ultraviolet, visible, infrared, or another wavelength or combination of wavelengths in the electromagnetic spectrum. This is accomplished in the case of wire grid array polarizers by adjusting the width, height, and/or spacing of the wires. This is accomplished in the case of nano-crystal polarizers through the choice of materials and processing parameters such as temperature. The optical channels may be optimized for ultraviolet, visible, infrared, or another wavelength or combination of wavelengths in the electromagnetic spectrum. In the case of fiberoptic channels, this is accomplished by the choice of materials, dopants, and core/clad ratios. For other kinds of optical channels, this is accomplished by the choice of materials and the design of any optical coatings used in the channels.

The substrate may be formed from a scratch-resistant material such as quartz, fused silica, or sapphire. The polarizer group may have a diamond-like, rhodium or other hard coating on its sample side to increase its scratch resistance. The substrate may be made of a material that has high transmittance in the spectral region of interest, such as glass or polymer that transmits broadband radiation. The substrate must not substantially fluoresce, must not impart significant birefringence, and for medical applications must be biocompatible.

Two of the polarizer pixels may have orthogonal polarization orientations. The optical probe may contain at least two discrete light-transmissive channels, with one polarizer pixel covering at least one light-receiving channel and a second, orthogonally-oriented polarizer pixel covering at least one light delivery channel and at least one light-receiving channel. The optical probe may contain at least three discrete light-transmissive channels, with one polarizer pixel covering at least one light-receiving channel and a second, orthogonally-oriented polarizer pixel covering at least one light delivery channel and at least one light-receiving channel. At least two light-receiving channels may be substantially tangent to a light delivery channel, or may be separated by certain distances that determine a sampling geometry, i.e., determine a specific volume of the sample from which scattered or reflected light is collected.

The polarizer pixels may be substantially circular, and may be substantially tangent to one another. The sample end of the probe may be substantially circular, and the polarizer pixels may be substantially tangent to the edge of the probe's sample end. The polarizer pixels may be substantially aligned with one another. The polarizer group may further comprise a non-polarized buffer zone separating at least two polarizer pixels from one another. The buffer zone may divide the polarizer group into two discrete portions.

By determining the physical characteristics of the optical channels, the location, the size and shape, or the center and peripheral shape of at least one optical channel may be specified. The optical instrument may contain a plurality of optical channels, and the determined physical characteristics may comprise the relative locations of the optical channels, and may further comprise the shapes of the optical channels. The physical characteristics may be determined by imaging the optical channels. Imaging the optical channels may comprise transmitting light along the optical channels. The physical characteristics may be determined using machine vision techniques, for example the use of image processing algorithms that calculate the center of blobs, the spacing of blobs, blob morphology, etc.

In one embodiment, this invention uses a lithographic electronic imaging process to create custom polarizer assemblies. Wire grid polarizers are one type of polarizer that may be created by the electronic imaging process. Lithographic processes are used to create semiconductors or printed circuit boards. There are two distinct types of lithography: those that use a mask to create patterns, and those that do not use a mask. Lithographic processes using masks include "photolithography", "optical lithography", and "X-ray lithography". A higher-resolution variant of this where air between the substrate and projection optics are replaced by water is called "immersion lithography". When a mask is used, patterns are created all at once on a substrate by projecting the image of a "master" pattern (mask). These methods generally have the highest throughput.

Lithography techniques that do not use masks are often referred to as "direct write" processes. These include "e-beam lithography", "laser assisted vapor deposition" and "ion-beam lithography". With these techniques, the pattern is formed point by point by "writing" with one or more laser beams.

At the heart of the lithographic process is an imageable photoresist that forms a pattern on a substrate. The photoresist may be used as either a positive or negative image of the desired final pattern, masking either the application of a new material onto the substrate, or masking an etchant used to strip away a thin film of material previously applied to the substrate.

The photoresist is first applied to the substrate, then exposed to patterned light and developed. The patterned light is either a positive or negative image of the desired result. The light exposure may either be a projection of a film or glass master, or may be directly written with a fine beam of light or ions. When developed, the portion of the resist exposed to light is hardened, and the unexposed portion is washed away.

A positive process may then be used to add a layer of material to the portion of the substrate left unprotected by the photoresist, or a negative process may be used to remove material unprotected by the photoresist.

Direct write processes can either be additive or ablative (subtractive) processes. In the ablative process, the entire workpiece is first coated in the desired material in a thin layer. A laser or other high-energy source is then used to ablate the material from the "background" of the image, leaving behind the desired pattern in the material. Ideally, the substrate is not one that can be ablated by the same high-energy source, although this is not completely necessary—in this case the depth of the ablation is controlled to remove only the top layer.

In the additive process, the workpiece starts out blank, and material is added via laser assisted vapor deposition. In this process, the workpiece is placed in a vacuum chamber. Vaporized material is then introduced into the chamber and is selectively deposited onto the workpiece only in areas that are exposed by a laser.

BRIEF DESCRIPTION OF THE DRAWINGS

Other objects, features and advantages will occur to those skilled in the art from the following description of the preferred embodiments and the accompanying drawings, in which.

DETAILED DESCRIPTION OF THE
PREFERRED EMBODIMENTS OF THE
INVENTION

Figure 1:
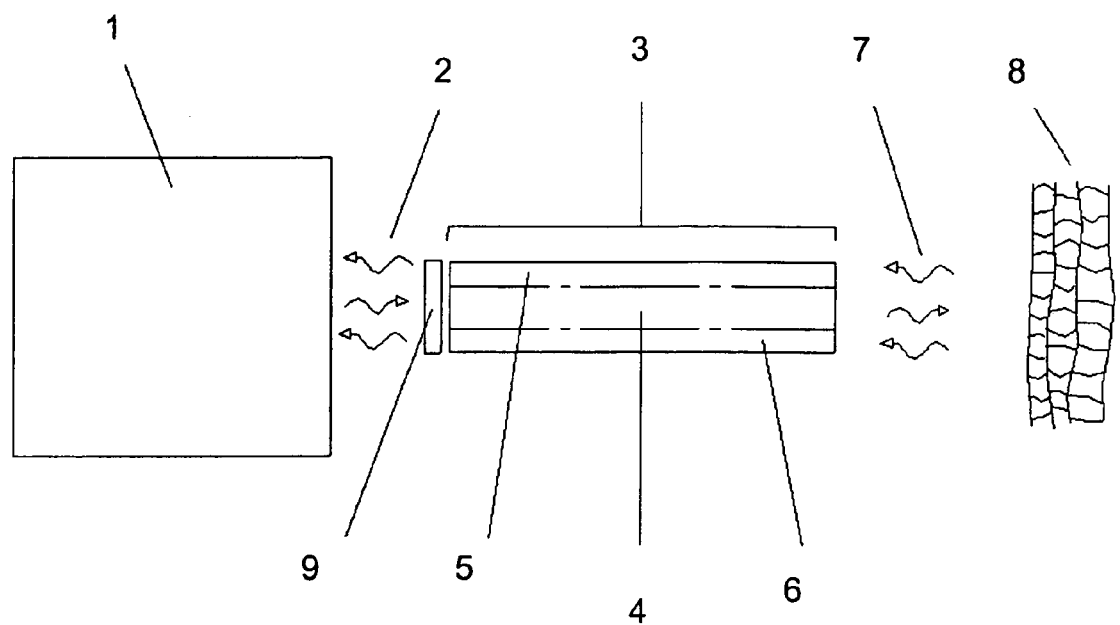
FIG. 1 is a schematic diagram of a prior art optical probe, in which polarizers are placed between the probe and an analysis instrument.
Figure 2:
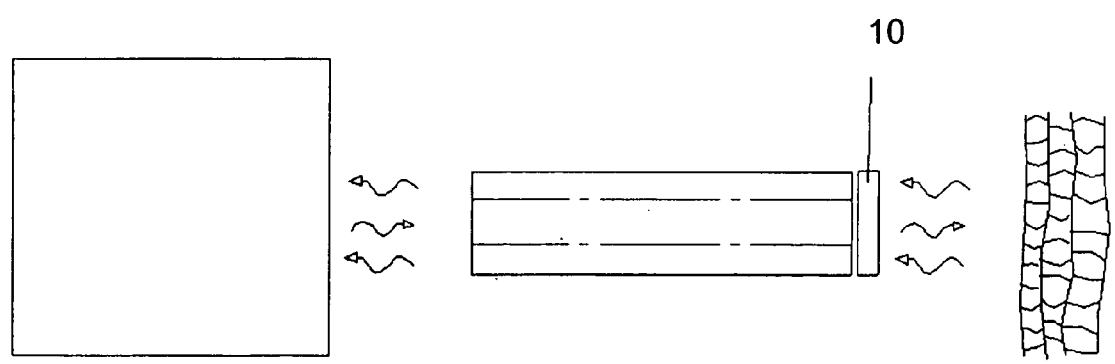
FIG. 2 is a schematic diagram of a preferred arrangement of a polarizer group made according to this invention on the sample end of an optical probe.

An embodiment of a polarizer group made according to the present invention is shown schematically in FIG. 2. Pixelated variably-polarizing polarizer group 10 is placed at the sample end of probe 3. Polarizer group 10 has one or more discrete, contiguous areas that are polarized in a particular polarization orientation, each such area (called a "pixel" herein) defining a single polarization axis. In most applications in which there are two pixels, the polarization axes of the pixels will be orthogonal with respect to one another, but any combination of polarization orientations may be employed. The pixels are typically sized, shaped and located to correspond to the size, shape and location at the probe sample end of the optical channels of the probe. Pixelated polarizer group 10 has a thickness that results in an acceptable level of Fresnel reflections in small diameter probes (defined as probes with a distal tip diameter of less than 25 mm, and preferably less than about 10 mm). Typically, polarizer group 10 is no more than about 200 microns thick.

This invention accomplishes the creation of patterns of polarizer "pixels" that can have any linear polarization orientation. These pixel patterns are compatible with the wire grid polarizer fabrication processes. They are also designed to make alignment to probe optical channels easy, cost-effective, and adaptable to a variety of probe configurations.

Figure 3:
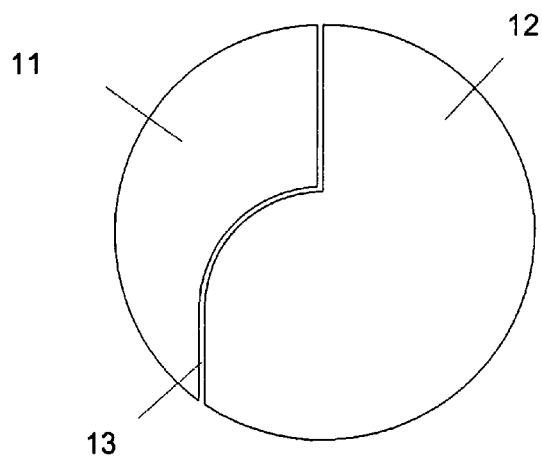
FIGS. 3–8 are schematic diagrams of alternative preferred polarizer groups made according to the invention.
Figure 4:
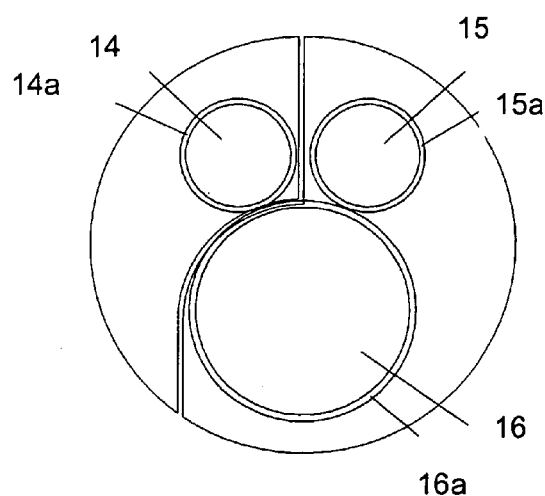

FIGS. 3 through 6 show a preferred exemplary embodiment of a polarizer group for this invention, showing a pixel pattern and its relationship to three optical channels. This pattern is optimized for use with one large delivery channel and two smaller collection channels. As shown in FIG. 3, the pattern consists of two pixels: the cross-polarized pixel 11 and the parallel-polarized pixel 12. As shown in FIG. 4, pixel 11 is designed to cover a single optical detection channel 14/14*a*, while pixel 12 is designed to cover the other detection channel 15/15*a* and the delivery channel 16/16*a*. In FIGS. 3 through 6 the optical channels are shown as optical fibers, with cores 14, 15 and 16 and outer cladding 14*a*, 15*a* and 16*a*, respectively. The optical channels could alternatively be formed from non-clad optical waveguides, or free-space optics. When clad fiberoptics are not used, 14, 15 and 16 represent the clear apertures of the channels, and 14*a*, 15*a*, and 16*a* (if present) represent space between the channels. To optimize signal-to-noise and the desired sampling volume, each collection channel is substantially tangent to the delivery channel. The two collection channels need not be tangent to one another.

Lithographic polarizer pixel production techniques can be used to create the wire grid array polarizer pixels. These techniques may require the sequential use of more than one mask. Inherent alignment errors between successive masks can be accounted for by spacing the pixels slightly with what is called a "buffer zone" (a non-polarized area between pixels). The buffer zone may divide the polarizer group in two. Advantageously, the pixels' borders can be placed so that these buffer zones lie over non-active areas of the probe face. For example, the pixel pattern can be arranged so that the buffer zone 13 (FIG. 3) lies between each of the fiber cores if optical fibers are used (or between the clear apertures of non-clad optical channels).

Light emitted from optical channel 16 passes through the polarizer and is linearly polarized with an orientation that is arbitrarily called "parallel". This light irradiates the sample. Backscattered rays are collected by the two detection channels 14 and 15. Channel 15 collects rays with the same polarization as the irradiating light (parallel) while channel 14 collects rays with orthogonal (or potentially some other) polarization orientation. The optical channels shown in FIG. 4 have typical relative sizes for this pixel pattern.

Figure 5:
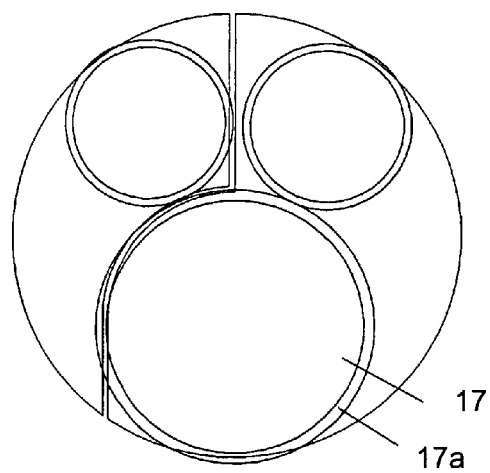
Figure 6:
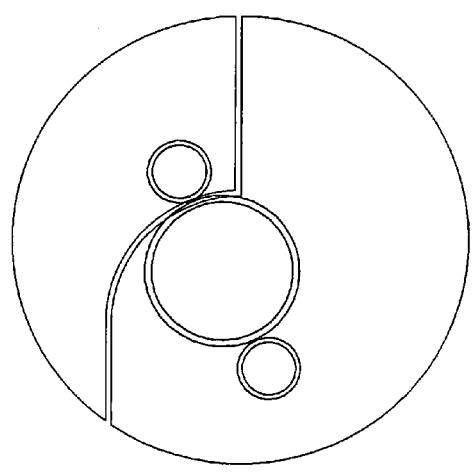

FIG. 5 shows optical channels of the largest possible size for this pixel pattern and a circular probe end. Note that all of the pixels in this case are about the same overall size as the sample end of the probe in order to maximize the number of polarizers that may be patterned in a lithographic fabrication mask. As long as the fiber core 17 is completely covered by the pixel, the cladding 17*a* may fall outside the pixel. FIG. 6 shows the same polarizer pattern used with arbitrarily small channels.

In FIGS. 4 through 6, the pixel pattern is arranged so that the collection channels 14 and 15 are substantially tangent with the delivery channel 16, and so that the buffer zone 13 overlays either the cladding, if the channels are fiberoptic, or between the clear apertures of the channels if non-clad waveguides or free space optics are used. Thus, this embodiment of a pixel pattern is designed to accommodate a substantial range of optical channel sizes. Alternative embodiments of this pixel pattern may be larger or smaller to accommodate a further increased range of optical channel sizes and combinations.

Figure 7:
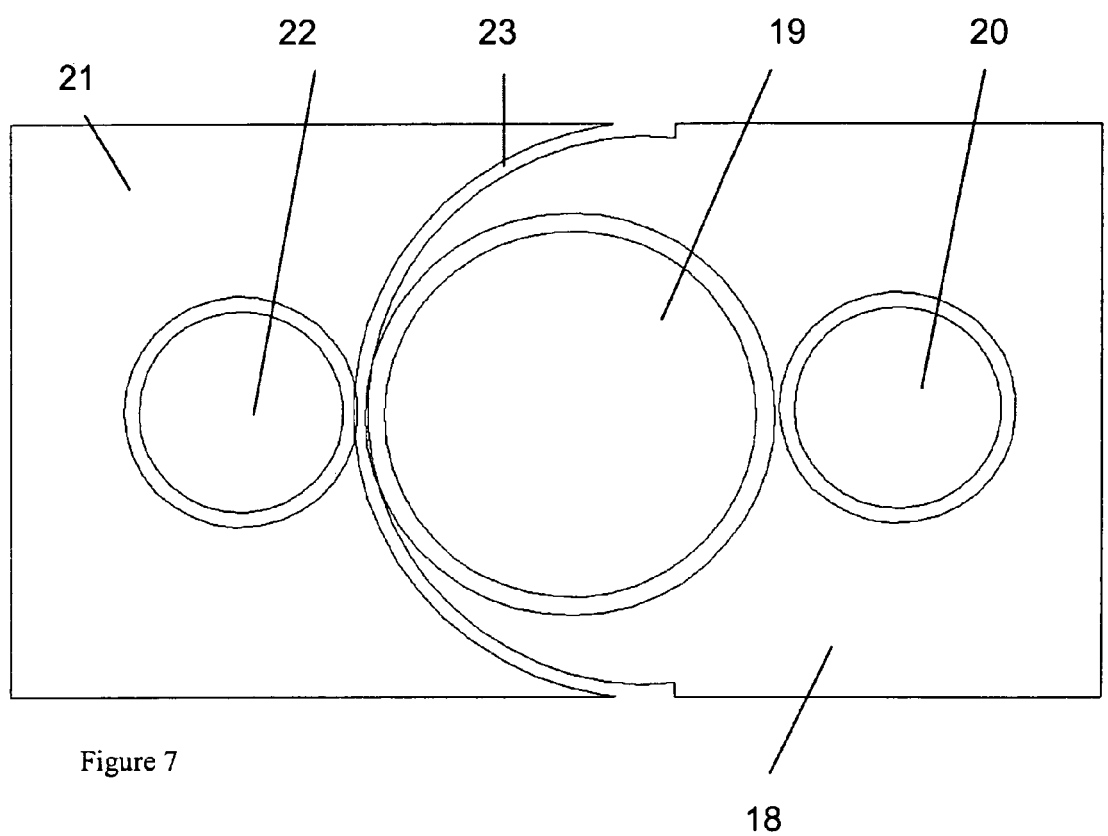
Figure 8:
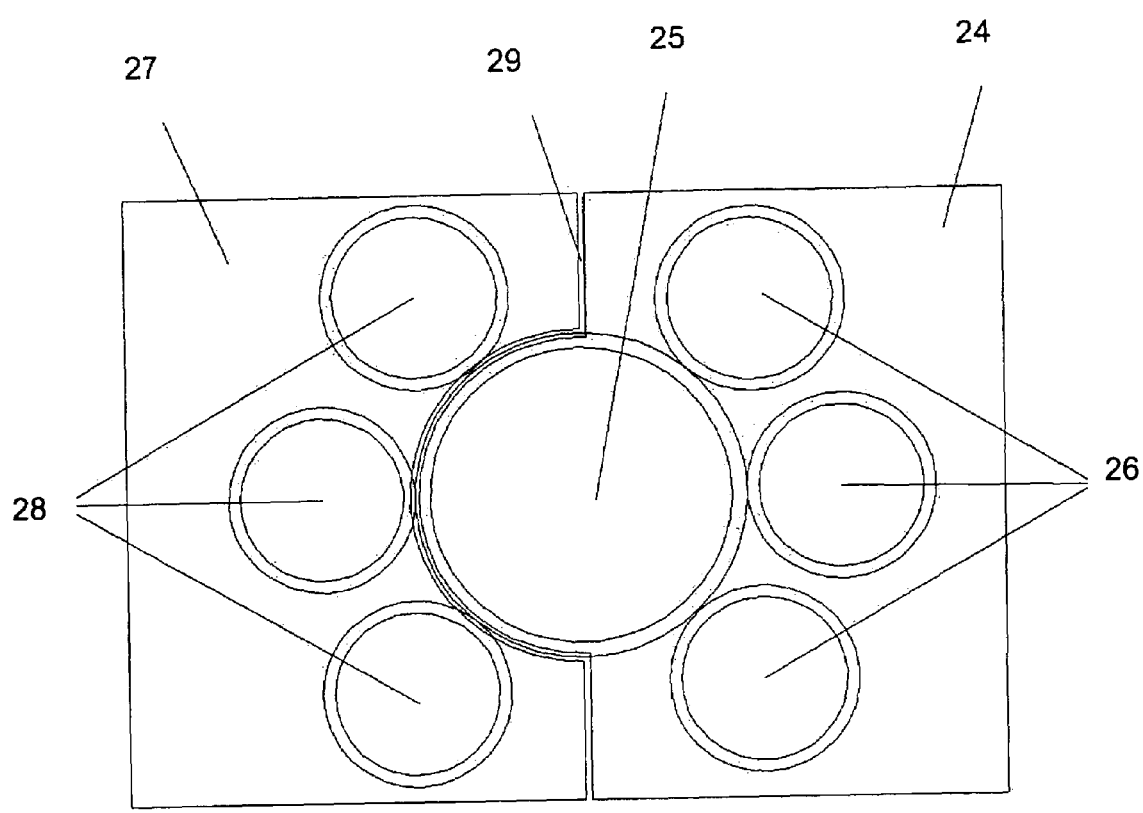

Alternative embodiments incorporate pixels of different shapes than the ones shown in FIGS. 3 through 6. For example, FIG. 7 shows a rectangular pixel pattern placed over three optical channels in a linear arrangement. Parallel polarization pixel 18 covers delivery channel 19 and detection channel 20. Orthogonal polarization pixel 21 covers detection channel 22. Buffer zone 23 is aligned over the cladding areas in the case of clad fiberoptic channels, and between the channel apertures when non-clad waveguides or free space optics are used. This pixel pattern is relatively insensitive to angular misalignment and is thus easier to assemble than some other patterns. FIG. 8 shows another alternative embodiment, this one optimized for a central delivery channel 25 surrounded by six substantially concentric collection channels (collectively labeled 26 and 28). Parallel polarization pixel 24 covers the delivery channel 25 and collection fibers 26. Cross polarization pixel 27 covers collection channels 28. A buffer zone 29 is aligned to overlay the inter-channel spaces and/or the cladding of the delivery channel.

In the embodiments described thus far, each pixel pattern is optimized for probes with certain fixed geometries. However, the shapes of the pixels are designed to accommodate normal assembly tolerances. The optical channels will not always be located at exactly the same places, but as long as the pixel pattern can be rotated in one axis and translated in 2 axes prior to mounting, alignment can be achieve for an acceptable range of assembly tolerances.

Figure 9:
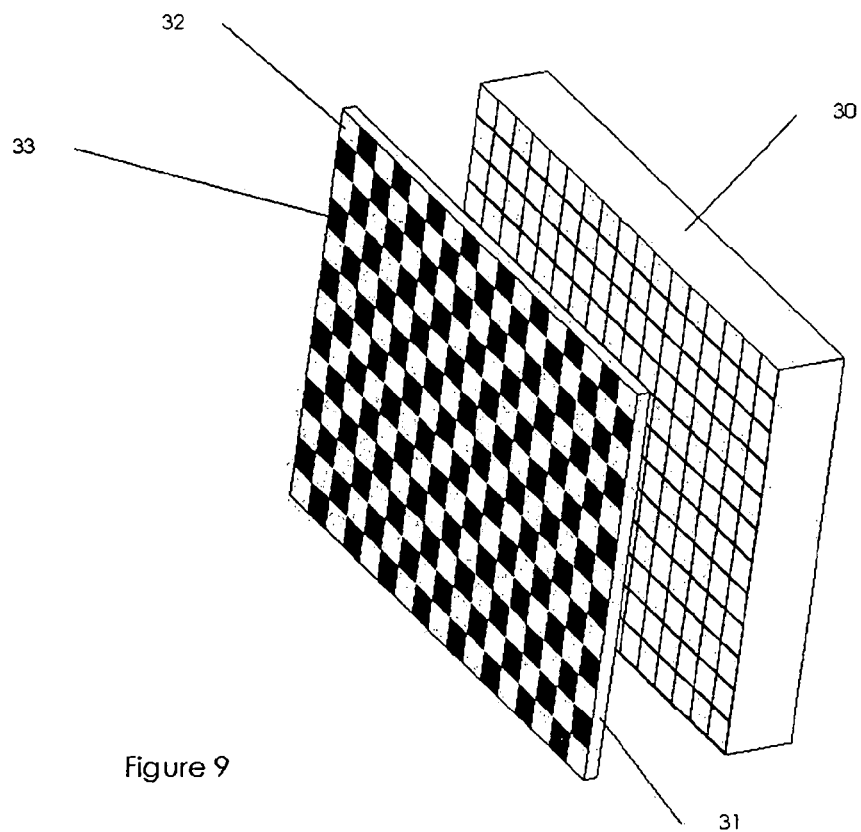
FIG. 9 is a schematic, exploded diagram of a variably-polarizing polarizer group made according to the invention.

The invention also describes the variably-polarizing polarizer groups per se. These polarizer groups polarize the light received by or emitted from a device, for example an image sensor. The polarizer group comprises an optically transmitting substrate such as described above, and one or more discrete polarizer pixels on a face of the substrate, each such polarizer pixel defining a polarization orientation, with the polarizer pixels together typically defining at least two different polarization orientations. When used with an image sensor, polarized imaging can be accomplished with a single image sensor. FIG. 9 shows a preferred embodiment. A detector array 30 may be comprised of a linear array of pixels or a two-dimensional array as shown. The detector may be a CCD imager, a CMOS imager, a HgCdTe detector, or another type of detector sensitive to some portion of the electromagnetic spectrum. The detector pixels may be contiguous to one another, or separated. A polarizer 31 consists of an array of polarizing pixels that matches the size and pitch of the pixels in the detector array. One group of polarizing pixels 32 have one orientation, while another group 33 has a different orientation. The two groups of pixels may be arranged in a checkerboard pattern as shown or in another pattern. For clarity of illustration, the polarizer is shown apart from the detector array. In use, these two components are closely mated. A color filter may also be incorporated into the design of FIG. 9 for the purpose of producing color images. The filter may be located either between polarizer 31 and the detector 30, or on the surface of polarizer 31 away from the detector 30. The color filter may have a mosaic or other pattern. A microlens array may also be incorporated into the design to improve collection efficiency of the detector. The microlens array may be located either between polarizer 31 and the detector 30, or on the surface of polarizer 31 away from the detector 30.

Figure 10:
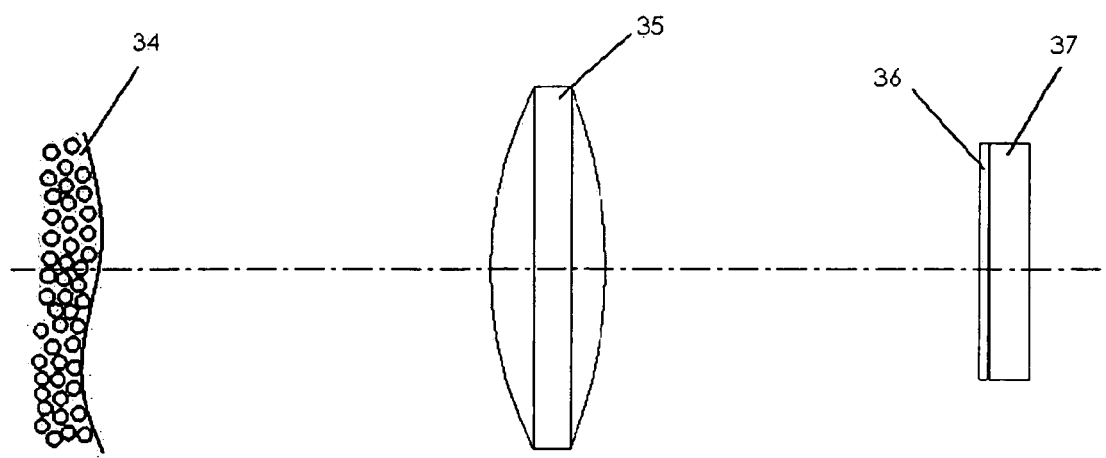
FIG. 10 schematically depicts a variably-polarizing polarizer group made according to the invention in use imaging a sample.

FIG. 10 shows a sample 34 being imaged by a lens 35. The image of the sample passes through polarizer 36, which is shown mounted onto detector 37. The signals from detector array 37 are capable of being processed in such a way that an image may be constructed from one group of pixels separate from the other group of pixels. Thus, electronic images of a sample with two or more different polarization states may be obtained. This technique has the further advantage that the multiple images are acquired simultaneously rather than sequentially. This is advantageous if the sample is moving because it minimizes motion artifacts, i.e., blurring, shifting, and other differences between the images that are caused by the motion. Simultaneous acquisition is also important for minimizing temporal artifacts if the characteristics of the sample are changing rapidly.

Figure 11:
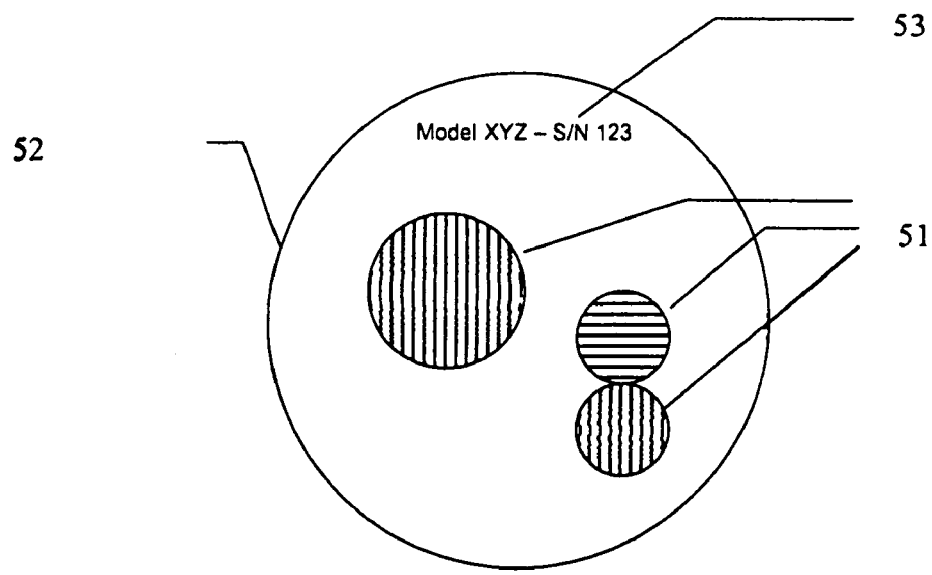
FIG. 11 is a schematic diagram of a single polarizer group manufactured by the processes of the invention.

FIG. 11 shows a polarizer group manufactured by the processes disclosed herein. Polarizer pixels 51 can have any size, shape or polarizer orientation. Polarizer group 52 consists of one or more polarizer pixels on a common substrate. The polarizer pixels of the group may have any shape, location, or orientation. Serial number or other code (e.g. bar code) 53 may be used during the manufacturing and/or assembly processes to indicate the intended application for the polarizer group. The serial number or bar code may be manually or automatically read by an optical reader during subsequent processes, and input into a computer or controller. The information may then be used during manual or automated assembly, alignment and testing of probes.

Figure 12:
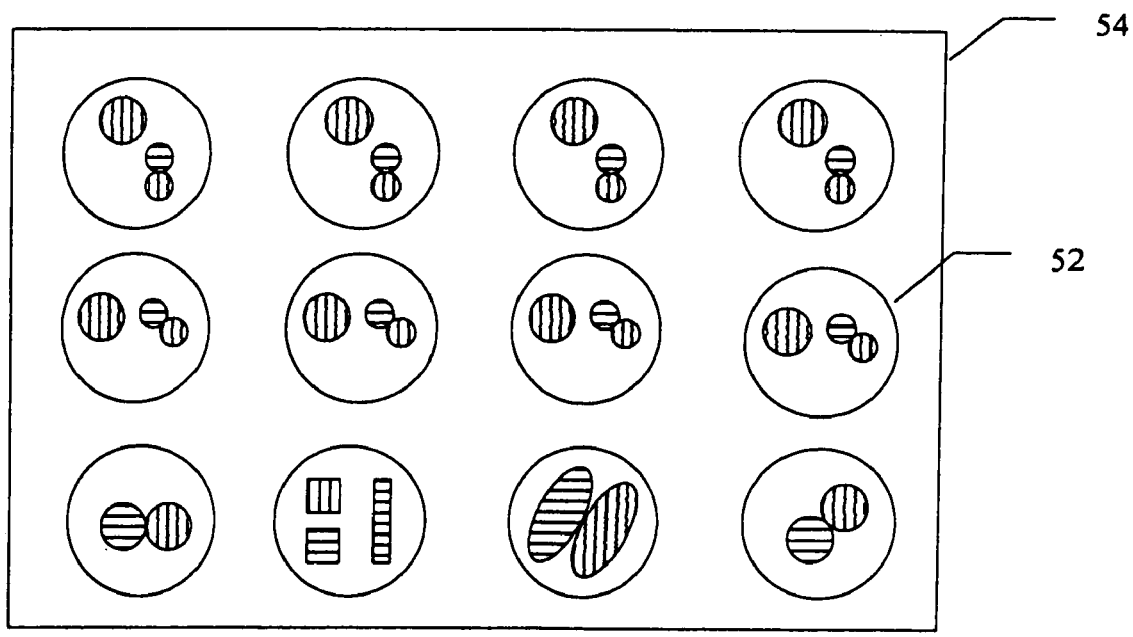
FIG. 12 is a schematic diagram of a workpiece containing multiple polarizer groups manufactured by the processes of the invention.

FIG. 12 shows a workpiece 54 consisting of multiple polarizer groups 52. It is likely that polarizer groups will be manufactured in quantity on workpieces several inches in diameter by the processes disclosed herein. Each group 52 may be the same, as shown in the top two rows of workpiece 54, or each may be different, as shown in the bottom row. Workpiece 54 in the preferred embodiment is imaged all at one time, and subsequently diced into individual polarizer groups. This technique is compatible with standard lithographic and integrated circuit manufacturing methods and thus has the potential to be very low cost.

The pixelated polarizer groups can be fabricated as follows. The substrate comprises a glass that transmits broadband radiation, does not fluoresce, does not impart significant birefringence, and is biocompatible. The substrate may alternatively be formed from a scratch-resistant material such as quartz, fused silica, or sapphire. Substrates should generally be less than about 200 microns thick. The polarizer group may have a diamond-like, rhodium or other hard coating on its sample side to increase its scratch resistance. The substrate preferably has the same size and shape as the sample end of the probe to which it is mounted (either adhesively or mechanically by clamping or the like). The polarizing pixels can be fabricated using any of the wire grid array techniques disclosed in U.S. Pat. No. 6,122,103, the disclosure of which is incorporated herein by reference.

In an alternative embodiment, dichroic polarizers formed with nano crystals are used instead of wire grid arrays. For example, manufacturer Optiva, Inc. has introduced a thinner variant of the sheet polarizer. It is a family of optical films that utilizes what Optiva calls "Thin Crystal Film™ (TCF) nano-material". It allows polarizers to be produced by coating a very thin molecularly-oriented layer film. A high performance polarizer coating results from shear force applied to the liquid as it is applied (i.e., a rolling, brushing, or wiping action). This shear force acts to create a preferred orientation, and "comb" the supramolecular strands created by self-assembly of the crystalline material. After shear force establishes a partial orientation, the liquid crystal property of the strands act to increase alignment. The deposition method produces a uniform polarizing coating of 7 to 15 microns thick when wet. After evaporation of water, a dry, thin crystalline polarizing layer remains with a thickness of 0.5–1 micron. Polarizing sheets of nearly any size may be fabricated. With proper fixturing, this film may be deposited onto substrates as thin as 10 microns. However, because of the requirement to "comb" the supramolecular strands, it is not feasible to create very small, adjacent pixels with orthogonal orientations. Any roller, brush or wiper would need to pass the edge of each pixel in order to orient the strands over the entire area of the pixel. If the pixels are adjacent to one another, the combing action on one pixel disturbs the crystal orientation established on the adjacent pixel. It is therefore necessary to create polarizer sheets that define only one orientation. These sheets are then cut into specific shapes with an automated scribe, laser, e-beam, water jet, or other microcutting technique. Using a vacuum manipulator, these pieces are then oriented onto the sample end of the optical probes. The non-coated sides of the pieces are bonded to the probe with an optically transparent adhesive. A UV-curing adhesive provides a nearly instant cure upon application of UV light. Alternatively, other optically transparent one- or two-part adhesives may be used. A cover glass may be fitted to seal the polarizers from environmental exposure.

Alternatively, instead of bonding the pieces directly onto the end of the probe, they may be bonded onto a secondary substrate, and the assembly bonded onto the probe in the same manner. The additional substrate may already be round, or it could be square or some other shape that is easy to form by scribing or dicing. In this case, after bonding to the probe, the substrate is preferably edged round by scribing or grinding. A third layer of substrate may also be used, so that the nano-crystal polarizer is "sandwiched" between two protective layers.

One aspect of this invention relates to the production of customized polarizer groups and workpieces of the types described above. A systems manufacturer may have many reasons for customizing polarizer group production. One may wish to correct for the alignment tolerances of the individual instruments being built by making a polarizer group that exactly conforms to each individual unit. Conversely, one may want to make instrument production more economical by using low-precision or even random methods for locating or assembling optical channels and correcting the results with a low-cost custom polarizer group. Or, a manufacturer may make many different models of a product, with a different polarization geometry for each, customized to the individual application (mass customization).

In the preferred embodiment of the invention, the manufacturer first determines physical characteristics of the optical channels, such as the size, shape, position, and orientation of the desired polarizer pixels. Depending on the application, the manufacturer will indicate the desired polarizer geometry by either creating a computer aided design (CAD) file or by capturing an image of the optical device, showing the individual optical channels over which the polarizer group will be placed. The required characteristics of the optical channels may also be determined using machine vision techniques, such as by calculating the centers and perimeter shapes of the distal ends of the optical channels. In this case, the pixel group geometry may be defined by an electronic data file such as a list of pixel diameters and center locations. A CAD file is most likely to be used where the customization is to accommodate different models (planned variation), while an image of the actual optical channels can be used for either planned variation or to accommodate manufacturing tolerances (random variation).

The manufacturer can add some sort of serial number or type indicator code to the file. This indicator will be placed in a non-active area, will be imaged and fabricated along with the polarizer data, and subsequently used to indicate the intended application for each individual polarizer group, or for more than one polarizer group.

After the size, shape and location of the polarizer pixels are determined, the manufacturer then adds the polarization orientation information to the file, either by annotating the CAD file, adding text or color to the image file, or some other means.

It will be apparent to those skilled in the art that the different types of manufacturing information may be easily combined. For example, one may illuminate the proximal ends of fiber probes with different colored light to indicate the desired polarization, resulting in a multicolored image of the distal (sample) end, providing all the information necessary to manufacture the polarizer assembly, including the size, shape and location of the optical channels, and the polarizer orientation for each channel.

The data file (CAD, photo, jpeg, database, other) is then transmitted to the polarizer manufacturer, who integrates the relevant data into CAD or imaging software to define the image file required to manufacture the polarizers. The outline of the size, shape and location of the individual polarizer pixels are incorporated directly into the tooling file of the CAD or imaging software. The data may be scaled or go through some other translation depending on the relationship between the file provided by the systems manufacturer and the input format of the CAD or imaging software used to create the image file.

The polarizer manufacturer then fills the outlines of the individual polarizer pixels with the tooling information necessary to create the polarizer. In the case of wire grid polarizers, this information is a series of "black" and "white" lines filling the area. The orientation of the black and white lines indicates the orientation of the resulting polarizer.

In the preferred embodiment, the final tooling CAD file ideally covers the entire workpiece and contains images of multiple polarizer groups. A polarizer group typically includes two or more polarizer pixels in proximity to each other on the workpiece that are intended to be left on a common substrate and used in a single optical system when the group is removed from the workpiece.

The polarizer manufacturer then manufactures the polarizer with a lithographic process. The process may use masks or direct writing. The following description is for a negative process, though either a positive or negative process may be used. A thin layer of metal is first deposited onto a sheet of appropriate substrate material. Photoresist is then applied over the entire workpiece and imaged with the tooling information contained in the CAD file. The photoresist may be exposed directly or indirectly, e.g. holographically, using either a glass or film master, or may be directly written with a laser. The photoresist is then processed, resulting in the removal of unexposed resist and the hardening of exposed resist. To produce pixels with an alternate orientation, the lithographic process is repeated for that group of pixels. This may be repeated several times. When the lithographic processes are complete, the workpiece will then show images of the individual polarizer pixels and polarizer groups. A close examination of each polarizer pixel will show microscopic series of parallel lines alternating between resist and bare metal. The direction of the lines indicates the polarizer orientation. The workpiece is then etched, resulting in the removal of all the exposed metal from the substrate. The photoresist protects the underlayer of deposited metal in selected areas. The residual photoresist is removed, and if necessary the individual polarizer pixels or polarizer groups are separated by the cutting of the substrate.

Those skilled in the art will recognize that a wire grid polarizer manufactured by lithographic means can be created in either a positive or negative process. That is, the photoresist may either protect an underlayer of metal while exposed metal is etched away, or the resist may protect an underlayer of clear substrate while metal is deposited on the exposed portions of the substrate.

If the polarizers are manufactured by the direct write ablative method, the substrate is again covered in a thin layer of metal. In this embodiment of the invention, the intermediate step of exposing and developing photoresist is eliminated, and the metal or other polarizer material is directly ablated with a laser, e-beam, or other high-energy source. In the areas external to the polarizer pixels, all material is ablated, while in the polarizer pixels, thin lines are ablated, leaving thin lines of material comprising the "wire grid". In this embodiment, the high-energy beam essentially "writes" the same image as would be used in the negative lithographic process.

If the polarizers are manufactured by the direct write additive method, the bare substrate is placed in a vacuum chamber for writing. In this embodiment of the invention, the vacuum chamber is filled with one or more gases or plasmas, and a laser directs the selective deposition of the desired material onto the surface of the substrate. In the areas external to the polarizer pixels, no writing or deposition occurs, while in the polarizer pixels, thin lines are imaged, depositing thin lines of material comprising the "wire grid". In this embodiment, the high-energy beam essentially writes the same image process.

While the creation of wire grid polarizers is the preferred embodiment, those skilled in the art will recognize that the invention may be applied to any polarizer pixel or polarizer group manufactured via an electronic imaging process.

Another embodiment of the invention may also be applied to conventional polarizer technologies other than those manufactured by electronic tooling processes. Normally the manufacturing process for these cannot yield pixilated polarizers small enough to be used in the applications described here. However, using the processes disclosed herein, polarizer pixels larger than the desired pixel size can be applied to a common substrate, and unwanted portions of the polarizers can then be ablated with a laser. This process may be applied to individual substrate layers, which are subsequently "sandwiched" together, or may be applied in steps to a single layer. The result is a polarizer assembly with individual polarizer pixels that are smaller than those which can be created using the native manufacturing process for these polarizer types.

Although specific features of the invention are shown in some drawings and not others, and described relative to some embodiments and not others, this is for convenience only and is not a limitation of the invention, which is defined solely by the claims. Other embodiments will occur to those skilled in the art and are within the following claims.

What is claimed is:

1. A method of creating a tooling design for the production of one or more polarizer groups, each such group comprising an optically transmitting substrate having thereon one or more discrete polarizer pixels, the polarizer group for use with an optical instrument comprising one or more optical channels, the method comprising:
   a. determining one or more physical characteristics of at least one optical channel of the optical instrument;
   b. based on the determined physical characteristics, defining one or more discrete polarizer groups to be created on the substrate, comprising defining for each such group:
      i. a location on the substrate for such polarizer group;
      ii. the size, shape and location within the group of each polarizer pixel of the group; and
      iii. the polarization orientation for each such polarizer pixel of the group; and
   c. establishing for each polarizer pixel tooling information that defines the pixel's polarization orientation.

2. The method of claim 1 wherein the polarizer pixels comprise wire grid arrays.

3. The method of claim 2 wherein the tooling information defines the orientation of the wire grid arrays.

4. The method of claim 1 further comprising mounting a polarizer group in close proximity to the optical channels of an optical instrument.

5. The method of claim 1 wherein the substrate is sufficiently thin so as to prevent cross-talk between optical channels caused by Fresnel reflections from the outer surface of the substrate.

6. The method of claim 1 wherein the substrate has an anti-reflection coating on one or more sides to decrease Fresnel reflections.

7. The method of claim 1, wherein the polarizer pixels are optimized for ultraviolet, visible, infrared, or another wavelength or combination of wavelengths in the electromagnetic spectrum.

8. The method of claim 1 wherein the substrate is formed from a scratch-resistant material.

9. The method of claim 8 wherein the scratch-resistant material is selected from the group of materials consisting of quartz, fused silica and sapphire.

10. The method of claim 1 wherein the substrate has a diamond-like, rhodium or other hard coating on at least one side to increase its scratch resistance.

11. The method of claim 1 wherein the substrate is made of a material that has high transmittance in the spectral region of interest, does not substantially fluoresce, does not impart significant birefringence, and is biocompatible.

12. The method of claim 1 wherein at least one polarizer group comprises at least two discrete polarizer pixels that have different polarization orientations.

13. The method of claim 1, wherein at least one polarizer pixel is substantially circular.

14. The method of claim 13 wherein at least two of the polarizer pixels of a group are substantially circular and substantially tangent to one another.

15. The method of claim 1 wherein at least one polarizer group further comprises a non-polarized buffer zone separating at least two polarizer pixels from one another.

16. The method of claim 15 wherein the buffer zone divides the group into two discrete portions.

17. The method of claim 1 wherein the shapes of the pixels facilitate alignment to the optical channels.

18. The method of claim 1 wherein the shapes of the pixels are designed to accommodate normal assembly tolerances of the optical channels.

19. The method of claim 1 wherein the determined physical characteristics comprise the location of at least one optical channel.

20. The method of claim 1 wherein the determined physical characteristics comprise the size and shape of at least one optical channel.

21. The method of claim 1 wherein the determined physical characteristics comprise the center and peripheral shape of at least one optical channel.

22. The method of claim 1 wherein the optical instrument comprises a plurality of optical channels, and the determined physical characteristics comprise the relative locations of a plurality of optical channels.

23. The method of claim 22 wherein the determined physical characteristics further comprise the shapes of the plurality of optical channels.

24. The method of claim 1 wherein the physical characteristics are determined by imaging the optical channels.

25. The method of claim 24 wherein imaging the optical channels comprises transmitting light along the optical channels.

26. The method of claim 1 wherein the physical characteristics are determined using machine vision techniques.

27. The method of claim 1 wherein the tooling design is created for a workpiece comprising a plurality of polarizer groups.

28. The method of claim 27 further comprising manufacturing the workpiece using a lithographic process.

29. The method of claim 28 wherein the lithographic process comprises using a mask.

30. The method of claim 29 wherein the mask defines a positive image of the desired result.

31. The method of claim 29 wherein the mask defines a negative image of the desired result.

32. The method of claim 28 wherein the lithographic process is a direct write process.

33. The method of claim 32 wherein the direct write process is additive.

34. The method of claim 32 wherein the direct write process is subtractive.

35. The method of claim 27 wherein the tooling information for each polarizer group includes a code identifying the group.

36. The method of claim 35 wherein the code is unique to each group.

37. The method of claim 35 wherein the code is capable of being read electronically by character recognition, or a bar code reader.

38. A method of creating a tooling design for the production of a workpiece comprising an optically transmitting substrate having thereon a plurality of polarizer groups, each polarizer group comprising a plurality of discrete polarizer pixels, the polarizer groups for use at the sample end of an optical instrument comprising a plurality of separate optical channels, the method comprising:

a. determining the relative locations and shapes of the sample ends of the optical channels of the optical instrument;
b. based on the determined relative locations and shapes of the optical channels, defining one or more discrete polarizer groups to be created on the substrate, comprising defining for each such group:
  i. a location on the substrate for such polarizer group;
  ii. the size, shape and location within the group of each polarizer pixel of the group; and
  iii. the polarization orientation for each such polarizer pixel of the group;
c. establishing for each polarizer pixel tooling information that defines the pixel's polarization orientation; and
d. manufacturing the workpiece from this tooling design using a lithographic process.

* * * * *